(12) United States Patent
Ogawa et al.

(10) Patent No.: US 12,109,232 B2
(45) Date of Patent: Oct. 8, 2024

(54) RADIATION/CHEMOTHERAPY SENSITIZER TO BE USED FOR INTRATUMORAL LOCAL INJECTION AND FOR CONTROLLED RELEASE OF HYDROGEN PEROXIDE WITH HYDROGEL AS CARRIER

(71) Applicant: KORTUC INC., Tokyo (JP)

(72) Inventors: Yasuhiro Ogawa, Kochi (JP); Shiho Tokuhiro, Kochi (JP); Hideki Oda, Kochi (JP); Norikazu Yokota, Kochi (JP); Ryo Akima, Kochi (JP)

(73) Assignee: KORTUC INC. (JP)

( * ) Notice: Subject to any disclaimer, the term of this patent is extended or adjusted under 35 U.S.C. 154(b) by 77 days.

(21) Appl. No.: 17/328,865

(22) Filed: May 24, 2021

(65) Prior Publication Data

US 2021/0401881 A1    Dec. 30, 2021

Related U.S. Application Data

(63) Continuation of application No. 14/767,939, filed as application No. PCT/JP2014/053542 on Feb. 14, 2014, now abandoned.

(30) Foreign Application Priority Data

Feb. 15, 2013   (JP) ................................ 2013-028413

(51) Int. Cl.
| | | |
|---|---|---|
| *A61K 33/40* | (2006.01) | |
| *A61K 9/00* | (2006.01) | |
| *A61K 9/06* | (2006.01) | |
| *A61K 41/00* | (2020.01) | |
| *A61K 45/06* | (2006.01) | |
| *A61K 47/42* | (2017.01) | |
| *A61N 5/10* | (2006.01) | |

(52) U.S. Cl.
CPC ............ *A61K 33/40* (2013.01); *A61K 9/0024* (2013.01); *A61K 9/06* (2013.01); *A61K 41/0038* (2013.01); *A61K 45/06* (2013.01); *A61K 47/42* (2013.01); *A61N 5/10* (2013.01)

(58) Field of Classification Search
None
See application file for complete search history.

(56) References Cited

U.S. PATENT DOCUMENTS

| | | | |
|---|---|---|---|
| 4,946,780 | A | 8/1990 | Hashimoto et al. |
| 5,639,787 | A | 6/1997 | Riordan et al. |
| 5,676,964 | A | 10/1997 | Della et al. |
| 6,387,413 | B1 | 5/2002 | Miyata et al. |
| 6,790,461 | B2 | 9/2004 | Miyata et al. |
| 6,825,186 | B1 | 11/2004 | Sessler et al. |
| 6,831,058 | B1 | 12/2004 | Ikada et al. |
| 7,014,860 | B1 | 3/2006 | Kawata et al. |
| 2004/0086453 | A1 | 5/2004 | Howes |
| 2006/0178342 | A1 | 8/2006 | Brown et al. |
| 2006/0251719 | A1 | 11/2006 | Tabata |
| 2006/0263395 | A1 | 11/2006 | Brown et al. |
| 2009/0074879 | A1 | 3/2009 | Braguti et al. |
| 2009/0269404 | A1 | 10/2009 | Ishiguro et al. |
| 2010/0010417 | A1 | 1/2010 | Ogawa et al. |

FOREIGN PATENT DOCUMENTS

| | | |
|---|---|---|
| CA | 2122519 | 10/1995 |
| CN | 1151118 | 6/1997 |
| EP | 0 341 745 | 12/1994 |
| JP | 63-123392 | 5/1988 |
| JP | 01-266102 | 10/1989 |
| JP | 02-234689 | 9/1990 |
| JP | 2003-252905 | 9/2003 |
| JP | 2004-203829 | 7/2004 |
| JP | 2004-277348 | 10/2004 |
| JP | 2005-325075 | 11/2005 |
| UA | 16 358 | 8/2006 |
| WO | 94/20115 | 9/1994 |
| WO | 99/10385 | 3/1999 |
| WO | 01/57093 | 8/2001 |
| WO | 2007/017176 | 2/2007 |
| WO | 2008/016163 | 2/2008 |
| WO | 2008/041514 | 4/2008 |
| WO | 2009/075329 | 6/2009 |
| WO | 2009/116556 | 9/2009 |

OTHER PUBLICATIONS

Extended European Search Report issued Sep. 14, 2016 in corresponding European Application No. 14752196.7.
Yasuhiko Tabata et al., "Biodegradation of Hydrogel Carrier Incorporating Fibroblast Growth Factor", Tissue Engineering, vol. 5, No. 2, Apr. 1, 1999, pp. 127-138.
Ryusaku Yamada et al., "Clinical Study of Porous Gelatin Sphere (YM 670) in Transcatheter Arterial Embolization", Jpn J Cancer Chemother, 32(10): 1431-1436, Oct. 2005, with English abstract.
Young (Journal of Controlled Release 109 (2005) 256-274).
Smith (Journal of the Mechanical Behavior of Biomedical Materials (2009) 264-271).
International Search Report issued May 13, 2014 in International Application No. PCT/JP2014/053542.
Masaya Yamamoto et al., "Controlled release by biodegradable hydro gels enhances the ectopic bone formation of bone morphogenetic protein", Biomaterials, 2003, vol. 24, pp. 4375-4383.
Yasuhiro Ogawa et al., Phase I study of a new radiosensitizer containing hydrogen peroxide and sodium hyaluronate for topical tumor injection: A new enzyme-targeting radiosensitization treatment, Kochi Oxydol-Radiation Therapy for Unresectable Carcinomas, Type II (KORTUC II), International Journal of Oncology, 2009, vol. 34, pp. 609-618.

(Continued)

*Primary Examiner* — Tigabu Kassa
(74) *Attorney, Agent, or Firm* — Mendelsohn Dunleavy, P.C.

(57) ABSTRACT

The present invention provides a radiation sensitizer or anti-cancer chemotherapy sensitizer that prevents the decomposition of hydrogen peroxide for a longer period of time, and that maintains its effect. The radiation sensitizer or anti-cancer chemotherapy sensitizer according to the present invention is characterized by using hydrogen peroxide together with a hydrogel containing a crosslinked gelatin gel.

7 Claims, 4 Drawing Sheets

(56) References Cited

OTHER PUBLICATIONS

Shiho Tokuhiro, et al., "Development of novel enzyme-targeting radiosensitizer (KORTUC) containing hydrogen peroxide for intratumoral injection for patients with low linear energy transfer-radioresistant neoplasms", Oncology Letters, 2010, vol. 1, pp. 1025-1028.
Yasuhiro Ogawa et al., "Safety and effectiveness of a new enzyme-targeting radio sensitization treatment (KORTUC II) for intratumoral injection for low-LET radioresistant tumors", International Journal of Oncology, 2011, vol. 39, pp. 553-560.
Wako Bio Window, 2011, No. 111, p. 19.
Yasuhiro Ogawa et al., "Mechanism of apoptotic resistance of human osteosarcoma cell line, HS-Os-1, against irradiation", International Journal of Molecular Medicine, 2003, vol. 12, pp. 453-458.
Yasuhiro Ogawa et al., "Apoptotic-resistance of the human osteosarcoma cell line HS-Os-1 to irradiation is converted to apoptotic-susceptibility by hydrogen peroxide: A potent role of hydrogen peroxide as a new radiosensitizer", International Journal of Molecular Medicine, 2003, vol. 12, pp. 845-850.
Yasuhiro Ogawa et al., "Immunocytochemical characteristics of human osteosarcoma cell line HS-Os-1: Possible implication in apoptotic resistance against irradiation", International Journal of Molecular Medicine, 2004, vol. 14, pp. 397-403.
Japanese Journal of Clinical Radiology, 2009, vol. 54, No. 12, pp. 1683-1688.
Yasuhiro Ogawa et al., "Mechanism of hydrogen peroxide-induced apoptosis of the human osteosarcoma cell line HS-Os-1", International Journal of Molecular Medicine, 2003, vol. 12, p. 459-463.
Merck Index 11th edition, 1989,p. 760-761.
Eiichi Fujihira et al., Kobunshi Hyaluronic Acid Sodium (NRD101) no Chintsu, Koensho Sayo, Basic Pharmacology & Therapeutics, 1994, vol. 22, No. 3, p. S703-S715 and English Abstract thereof.
Hajime Yamamoto et al., Shokuyo Hyaluronic Acid (ECM-E) no Chintsu Sayo oyobi Sosho Chiryo Sokusyhin Koka, Medicine and Biology, 1999, vol. 139, No. 6, p. 253-258 and partial English translation.
Theodore L. Phillips, "Chemical Modifiers of Cancer Treatment", International Journal of Radiation Oncology Biol. Phys., 1984, vol. 10, p. 1791-1794.
C. Norman Coleman, "Hypoxic Cell Radiosensitizers: Expectantions and Progress in Drug Developement", International Journal of Radiation Oncology Biol. Phys., 1985, vol. 11 p. 323-329.
Renato Toffanin et al., NMR studies of oligasccharides derived from hyaluronate: complete assignment of IH and 13C NMR spectra of aqueous di- and tetra-saccharides, and comparison of chemical shifts for oligosaccharides of increasing degree of polymerisation, Carbohydrate Research, 1993, vol. 245, p. 113-128.
Mary K. Cowman et al., "13C-NMR Studies ofHyaluronan: Conformational Sensitivity to Varied Environments", Macromolecules, 1996, vol. 29, p. 2894-2902.
John R. Haaga et al., "Combined Tumor Therapy by Using Radiofrequency Ablation and 5-FU-Laden Polymer implants: Evaluation in Rats and Rabbits", Radiology, 2005, vol. 237, p. 911-918.
Eric J. Hall et al., Radio biology for the Radiologist (Sixth Edition), 2006, p. 419-431.
Chikako Y omota, "Evalution of Molecular Weights of Hyaluronate Preparations by Multi-Angle Laser Light Scattering", Bull. Natl. Inst. Health Sci., 2003, vol. 121, p. 030-033 and English Abstract thereof.
International Search Report issued Nov. 20, 2007, in the International (PCT) Application PCT/JP2007/068376.
Chinese Office Action with English translation dated Jan. 14, 2011, in Chinese Application No. 200780043347.2.
Supplementary European Search Report dated Feb. 28, 2011, in European Application No. 07807718.7.
Clinical Trail Results, "When Combined with Chemotherapy, Bevacizumab is Associated with Increased Risk of Death", Adapted from NCI Cancer Research Bulletin (Mar. 30, 2011).
Ogawa et al., Int. J. Radiation Oncology Biol. Phys., vol. 80, No. 1, p. 111-118 (2011).
Mukai et al., "Final Results of a Safety and Efficacy Trial of Preoperative Sequential Chemoradition Therapy for the Nonsurgical Treatment of Early Breast Cancer: Japan Clinical Oncology Group Study JCOG0306", Oncology, vol. 85, p. 336-341 (2013).
Ogawa et al., 20th Annual Meeting on the Sensitization of Cancer Treatment, Kochi Prefectural Culture Hall (Jun. 7, 2014).
Haller et al., "Oxygen embolism after hydrogen peroxide irrigation of a vulvar abscess", British J. Anesthesia, vol. 88, No. 4, p. 597-599 (2002).
Hall et al., Radiobiology for the Radiologist, 6th Edition, Chapter 25, "Radiosensitizers and Bioreductive Drugs", p. 419-431 (2006).
Hecht Jr. et al., Clin. Cancer Res., 2003; 9: p. 555-561.
International Preliminary Report on Patentability mailed Jan. 19, 2015, issued in corresponding International Application No. PCT/JP2014/053542, filed Feb. 14, 2014, 12 pages.

At the start of measurement 6 hours after the start of measurement 24 hours after the start of measurement 10 days after the start of measurement

RADIATION/CHEMOTHERAPY SENSITIZER TO BE USED FOR INTRATUMORAL LOCAL INJECTION AND FOR CONTROLLED RELEASE OF HYDROGEN PEROXIDE WITH HYDROGEL AS CARRIER

CROSS-REFERENCES TO RELATED APPLICATIONS

This application is a continuation of U.S. Application No. 14/767,939, filed Aug. 14, 2015, which is a National Stage of PCT/JP2014/053542, filed Feb. 14, 2014, which claims the benefit of Japanese Application No. 2013-028413, filed Feb. 15, 2013, the disclosures of which are each expressly incorporated herein by reference in their entirety.

TECHNICAL FIELD

The present invention relates to a sensitizer for enhancing a therapeutic effect of radiation or an anti-cancer agent on a tumor, and particularly to a sustained-release radiation sensitizer or anti-cancer chemotherapy sensitizer injected into a tumor area upon irradiation with radiation or administration of an anti-cancer agent. The present invention further relates to an anti-cancer therapy using the sensitizer.

BACKGROUND ART

As a method for locally treating malignant tumors, radiotherapy is second after surgical operations. Because radiotherapy can be applied to elderly patients and also enables normal organs and tissues to be conserved, the number of patients treated with this method has recently been increasing very rapidly. However, linear-accelerator-generated high-energy X-rays and electron beams that are currently used commonly for radiotherapy are low linear energy transfer (LET) radiation, which has a relatively low biological effect. Accordingly, linear-accelerator-based radiotherapy has little effect on tumors such as malignant melanoma, various types of sarcoma, and glioblastoma multiform. Because locally advanced cancers that have grown to several centimeters or more have many hypoxic cancer cells or contain large amounts of antioxidative enzymes, such cancers are not only resistant to radiation but also often resistant to anti-cancer chemotherapy.

The present inventors previously confirmed that using hydrogen peroxide together with radiotherapy or anti-cancer chemotherapy is effective for such tumors that are resistant to radiotherapy or anti-cancer chemotherapy (see, for example, Non-patent Literature (NPL) 1 to NPL 3.)

Further, the present inventors previously confirmed that using hydrogen peroxide together with hyaluronic acid or a salt thereof is most effective for intratumorally administering hydrogen peroxide, which is highly irritant to the affected area and is prone to decompose in tumors (see, for example, Patent Literature (PLT) 1, and NPL 4 to NPL 7).

CITATION LIST

PTL

PTL 1: WO2008/041514
PTL 2: JP2004-203829A
PTL 3: JP2005-325075A

NPL

NPL 1: Yasuhiro Ogawa et al., Mechanism of apoptotic resistance of human osteosarcoma cell line, HS-Os-1, against irradiation, International Journal of Molecular Medicine 12: 453-458, 2003

NPL 2: Yasuhiro Ogawa et al., Apoptotic-resistance of human osteosarcoma cell line HS-Os-1 to irradiation is converted to apoptotic-susceptibility by hydrogen peroxide: A potent role of hydrogen peroxide as a new radiosensitizer, International Journal of Molecular Medicine 12: 845-850, 2003

NPL 3: Yasuhiro Ogawa et al., Immunocytochemical characteristics of human osteosarcoma cell line HS-Os-1: Possible implication in apoptotic resistance against irradiation, International Journal of Molecular Medicine 14: 397-403, 2004

NPL 4: Yasuhiro Ogawa et al., Phase I study of a new radiosensitizer containing hydrogen peroxide and sodium hyaluronate for topical tumor injection: A new enzyme-targeting radiosensitization treatment, Kochi Oxydol-Radiation Therapy for Unresectable Carcinomas, Type II (KORTUC II), International Journal of Oncology 34: 609-618, 2009

NPL 5: Ryo Akama, Yasuhiro Ogawa, et al., Experimental Study on Radiation Sensitizing Effect of Intratumorally Administering Hydrogen Peroxide to Mouse-transplanted Tumor, Usefulness of Adding Hyaluronic Acid, Clinical Radiation Vol. 54, No. 12, 2009

NPL 6: Shiho Tokuhiro, Yasuhiro Ogawa, et al., Development of a novel enzyme-targeting radiosensitizer (KORTUC) containing hydrogen peroxide for intratumoral injection for patients with low linear energy transfer-radioresistant neoplasms, Oncology Letters 1: 1025-1023, 2010

NPL 7: Yasuhiro Ogawa and et al., Safety and effectiveness of a new enzyme-targeting radiosensitization treatment (KORTUC II) for intratumoral injection for low-LET radioresistant tumors, International Journal of Oncology 39: 553-560, 201

SUMMARY OF INVENTION

Technical Problem

The radiation sensitizer or anti-cancer chemotherapy sensitizer comprising hydrogen peroxide, and hyaluronic acid or a salt thereof (hereinafter also referred to as "KORTUC") that was previously developed by the present inventors must be locally injected into a tumor in the patient under ultrasonographic guidance twice a week during radiotherapy or anti-cancer chemotherapy. Therefore, when the sensitizer is injected, the patient to be treated has a heavy physical and mental burden, such as pain, and doctors who inject the sensitizer, as well as doctors or the like who are in charge of ultrasonography, are also physically burdened and pressured by time. Even when KORTUC is used, the highest radiation sensitizing effect with the highest partial pressure of oxygen in tumors is obtained within 24 hours after injecting the sensitizer; therefore, irradiation with radiation or anti-cancer chemotherapy must be performed immediately after injecting the sensitizer.

In order to solve the above problem, an object of the present invention is to provide a sensitizer that is for enhancing a therapeutic effect of radiation or an anti-cancer agent on a tumor and that can prevent the decomposition of hydrogen peroxide for a longer period of time and maintains its effect.

Solution to Problem

The present inventors conducted extensive research to solve the above problem. They found that when hydrogen peroxide is used together with a hydrogel comprising a crosslinked gelatin gel, hydrogen peroxide administered into the body can be significantly inhibited from decomposition due to the function of antioxidants and can maintain the effect of hydrogen peroxide administration for a longer period of time than KORTUC. The inventors further found that even when the frequency of hydrogen peroxide administration is reduced, using hydrogen peroxide together with a hydrogel comprising a crosslinked gelatin gel can provide more potent radiation sensitizing effects and anti-cancer chemotherapy sensitizing effects than using KORTUC, due to the long-term sustained release of hydrogen peroxide immersed in the hydrogel.

The present invention has been accomplished based on the above findings and includes the following.

I. Sensitizer for Enhancing Therapeutic Effect of Radiation or Anti-cancer Agent on Tumor I-1. A sensitizer for enhancing a therapeutic effect of radiation or an anti-cancer agent on a tumor, the sensitizer comprising a combination of:
(a) hydrogen peroxide and
(b) a hydrogel comprising a crosslinked gelatin gel,
and the sensitizer being locally administered to a tumor area.

I-2. The sensitizer according to Item I-1, wherein the tumor is resistant to treatment using radiation or an anti-cancer agent.

I-3. The sensitizer according to Item I-1 at I-2, wherein a first administration of the sensitizer is performed during a period from 3 days before a first irradiation with radiation or a first administration of the anti-cancer agent until the start of the irradiation or the administration of the anti-cancer agent.

I-4. The sensitizer according to Item I-3, wherein a second administration of the sensitizer is performed 5 to 14 days after the first administration of the sensitizer.

I-5. The sensitizer according to any one of Items I-1 to I-4, wherein the crosslinked gelatin gel is prepared from a gelatin having an isoelectric point of 4.5 to 5.5.

I-6. The sensitizer according to any one of Items I-1 to I-5, wherein the crosslinked gelatin gel has a water content of 92 to 99.7%.

I-7. The sensitizer according to any one of Items I-1 to I-6, which, in the form of a final formulation, is administered in an amount of 0.1 to 10 mg, on a dry weight basis of the crosslinked gelatin gel, per 200 $mm^3$ of the tumor volume.

I-8. The sensitizer according to any one of Items I-1 to I-7, which, in the form of the final formulation, contains hydrogen peroxide in an amount of 0.01 to 3.5 wt. %.

II. Method for Treating Tumor

II-1. a method for treating a tumor, comprising the steps of:
(1) locally administering to a tumor area a sensitizer comprising a combination of (a) hydrogen peroxide and (b) a hydrogel comprising a crosslinked gelatin gel; and
(2) irradiating the tumor area with radiation or administering an anti-cancer agent to a patient suffering from the tumor.

II-2. The method according to Item II-1, wherein the tumor is resistant to treatment using radiation or an anti-cancer agent.

II-3. The method according to Item II-1 or II-2, wherein a first administration of the sensitizer is performed during a period from 3 days before a first irradiation with radiation or a first administration of the anti-cancer agent until the start of the irradiation or the administration of the anti-cancer agent.

II-4. The method according to Item II-3, wherein a second administration of the sensitizer is performed 5 to 14 days after the first administration of the sensitizer.

II-5. The method according to any one of Items II-1 to II-4, wherein the crosslinked gelatin gel is prepared from a gelatin having an isoelectric point of 4.5 to 5.5.

II-6. The method according to any one of Items II-1 to II-5, wherein the crosslinked gelatin gel has a water content of 92 to 99.7%.

II-7. The method according to any one of Items II-1 to II-6, wherein the sensitizer, in the form of a final formulation, is administered in an amount of 0.1 to 10 mg, on a dry weight basis of the crosslinked gelatin gel, per 200 $mm^3$ of the tumor volume.

II-8. The method according to any one of Items II-1 to II-7, wherein the sensitizer, in the form of the final formulation, contains hydrogen peroxide in an amount of 0.01 to 3.5 wt. %.

III. Composition for Treating Tumor Using Radiation or Anti-cancer Agent

III-1. A composition for treating a tumor using radiation or an anti-cancer agent, the composition comprising a combination of
(a) hydrogen peroxide and
(b) a hydrogel, comprising a crosslinked gelatin gel,
and the composition being locally administered to a tumor area.

III-2. The composition according to Item III-3, wherein the turner is resistant to treatment using radiation or an anti-cancer agent.

III-3. The composition according to Item III-1 or III-2, wherein a first administration of the sensitizer is performed during a period from 3 days before a first irradiation with radiation or a first administration of the anti-cancer agent until the start of the irradiation or the administration of the anti-cancer agent.

III-4. The composition according to Item III-3, wherein a second administration of the sensitizer is performed 5 to 14 days after the first administration of the sensitizer. III-5. The composition according to any of Items III-1 to III-4, wherein the crosslinked gelatin gel is prepared from a gelatin having an isoelectric point of 4.5 to 5.5.

III-6. The composition according to any of Items III-1 to III-5, wherein the crosslinked gelatin gel has a water content of 92 to 99.7%.

III-7. The composition according to any of Items III-1 to III-6, which, in the form of a final formulation, is administered in an amount of 0.1 to 10 mg, on a dry weight basis of the crosslinked gelatin gel, per 200 $mm^3$ of the tumor volume.

III-8. The composition according to any of Items III-1 to III-7, which, in the form of a final formulation, contains hydrogen peroxide in an amount of 0.01 to 3.5 wt. %.

IV. Use in the Manufacture of Sensitizer for Enhancing Therapeutic Effect of Radiation or Anti-cancer Agent on Tumor IV-1. Use of a composition for local administration to a tumor area in the manufacture of a sensitizer for enhancing a therapeutic effect of radiation or an anti-cancer agent on a tumor, the composition comprising a combination of the following components (a) and (b):
(a) hydrogen peroxide; and
(b) a hydrogel comprising a crosslinked gelatin gel.

IV-2. The use according to Item IV-1, wherein the tumor is resistant to treatment using radiation or an anti-cancer agent.

IV-3. The use according to Item IV-1 or IV-2, wherein a first administration of the sensitizer is performed during a period from 3 days before a first irradiation with radiation or a first administration of the anti-cancer agent until the start of the irradiation or the administration of the anti-cancer agent.

IV-4. The use according to Item IV-3, wherein a second administration of the sensitizer is performed 5 to 14 days after the first administration of the sensitizer.

IV-5. The use according to any one of Items IV-1 to IV-4, wherein the crosslinked gelatin gel is prepared from a gelatin having an isoelectric point of 4.5 to 5.5.

IV-6. The use according to any of Items IV-1 to IV-5, wherein the crosslinked gelatin gel has a water content of 32 to 99.7%.

IV-7. The use according to any of Items IV-1 to IV-6, wherein the sensitizer, in the form of a final formulation, is administered in an amount of 0.1 to 10 mg, on a dry weight basis of the crosslinked gelatin gel, per 200 mm$^3$ of the tumor volume.

IV-8. The use according to any of Items IV-1 to 1V-7, wherein the sensitizer, in the form; of the final formulation, contains hydrogen peroxide in an amount of 0.01 to 3.5 wt. %.

Advantageous Effects of Invention

According to the present invention, sensitivity to the effects of radiotherapy or anti-cancer chemotherapy can be increased even when irradiation by radiation or administration of an anti-cancer agent is not performed immediately after administration of the sensitizer. Further, the present invention can prolong turner growth inhibition effects per dose of radiation for a long period of time, even compared to KORTUC, and provide more potent tumor growth inhibition effects than KORTUC. Furthermore, while KORTUC must be injected into an affected area twice a week to provide effects, the sensitizer according to the present invention is effective with administration once a week at most, thus reducing physical, mental, and time burden on the person to be treated.

Furthermore, the present invention can provide more potent tumor growth inhibition effects and reduce the risk of tumor recurrence, even compared to KORTUC.

BRIEF DESCRIPTION OF DRAWINGS

FIG. 6 shows the effects on tumor volume of irradiation with radiation performed 48 hours after the administration of each sensitizer to a tumor. The tumor volume was measured on day 37 after the administration of each sensitizer (on day 35 after irradiation with radiation). The control refers to a group that was only irradiated with radiation. KORTUC refers to a group to which KOURTUC was administered and that was irradiated with radiation. PI5-100 refers to a group to which 100 μl of the sensitizer obtained in Formulation Example 1 was administered and that was irradiated with radiation. PI5-30 refers to a group to which 30 μl of the sensitizer obtained in Formulation Example 1 was administered and that was irradiated with radiation. PI9-2 refers to a group to which the sensitizer obtained in Formulation Example 2 was administered in an amount of 2 mg, on a dry weight basis of PI-9, and that was irradiated with radiation. PI9-0.6 refers to a group to which the sensitizer obtained in Formulation Example 2 was administered in an amount of 0.6 mg, on a dry weight basis of PI-9, and that was irradiated with radiation.

DESCRIPTION OF EMBODIMENTS

I. Sensitizer for Enhancing Therapeutic Effect of Radiation or Anti-cancer Agent or Tumor I-1. Composition of Sensitizer A feature of the sensitizer for enhancing a therapeutic effect of radiation or an anti-cancer agent on a tumor according to the present invention (sometimes simply referred to as the "sensitizer" in this specification) is that the sensitizer comprises (a) hydrogen peroxide and (b) a hydrogel comprising a crosslinked gelatin gel.

In the present invention, "the sensitizer for enhancing a therapeutic effect of radiation or an anti-cancer agent" refers to a pharmaceutical composition that can be locally administered to a tumor area before, simultaneously with, or after irradiation with radiation in radiotherapy (irradiation with radiation) or administration of an anti-cancer agent in anti-cancer chemotherapy (administration of an anti-cancer agent), and that can increase the effect of radiotherapy or anti-cancer chemotherapy on the tumor area.

In the present invention, "tumor" refers to tuners in general, regardless of whether benign or malignant, or epithelial or non-epithelial. Malignant tuners are preferable. Although the tumor is not particularly limited in sensitivity to therapy using radiation and/or an anti-cancer agent, tumors that are resistant to therapy using radiation or an anti-cancer agent are preferable.

In the present invention, "tumor area" refers to a tumor tissue in which tumor cells are mainly present. The tumor tissue includes tissue in which tumor cells and normal cells and/or normal tissue are present together. When tumor cells and normal cells and/or normal tissue are present together, the volume or number of tumor cells relative to that of normal cells and/or normal tissue is not particularly limited.

Therapeutic effects can be evaluated by using general evaluation methods, such as the percentage of tumor tissue shrinkage, patient survival rate, and recurrence rate after treatment.

The effect of linear-accelerator-based radiotherapy on tumor cells depends about 70% on the production of active oxygen species, such as hydroxyl radicals. The mechanisms of various anti-cancer agents (carcinostatic agents) also have this point in common. Therefore, a substance that increases sensitivity to radiotherapy effects also increases sensitivity to anti-cancer chemotherapy effects on tumors at the same time.

"Hydrogen peroxide" as used in the present invention refers to hydrogen peroxide molecules ($H_2O_2$; molecular weight of 34) unless otherwise specified.

"Aqueous hydrogen peroxide solution" refers to hydrogen peroxide dissolved in distilled water in the Japanese Pharmacopoeia or the like unless otherwise specified. The concentration of hydrogen peroxide in the hydrogen peroxide solution is 0.1 to 30 w/v %, and preferably 2.5 to 30 w/v %.

"Oxydol" as used in this specification refers to oxydol in accordance with the Japanese Pharmacopeia and is an aqueous hydrogen peroxide solution containing 2.5 to 3.5 w/v % of hydrogen peroxide.

In this specification, w/v % refers to weight/volume percent concentration unless otherwise specified.

Gelatin that is a starting material for the "crosslinked gelatin gel" used in the present invention can be obtained by denaturing collagen that can be obtained from various body parts, such as skin, bones, tendons, ligaments, fins, and tails, of various kinds of animal species, such as cows, pigs, and fish, by various treatments such as alkaline hydrolysis, acid hydrolysis, and/or enzymatic decomposition. The gelatin is preferably a bovine- or porcine-derived gelatin, and particularly preferably bovine-derived gelatin.

The gelatin may be naturally occurring collagen or one obtained by denaturing collagen produced by genetic recombination technology using the following method.

The method for obtaining gelatin is not particularly limited. Gelatin may be extracted from bones, etc., of the animals mentioned above, or commercially available products such as those obtained from Nitta Gelatin Inc., Nippi Inc., and Gunze Ltd. may be used. Gelatin that does not contain any endotoxin is preferable.

The gelatin may be, for example, alkali-treated gelatin (acidic gelatin) with an isoelectric point of 4.5 to 5.5, and preferably 4.6 to 5.0; or acid-treated gelatin (alkaline gelatin) with an isoelectric point of 7.0 to 10.0, and preferably 8.0 to 9.0. Acidic gelatin with an isoelectric point of 4.8 to 5.0 is preferable.

Acidic gelatin can be obtained by treating collagen using lime or the like according to a usual method for about 2 to 3 months. The deamidation rate after alkali treatment is about 98 to 100%.

Alkaline gelatin can be obtained by treating collagen using an inorganic acid such as hydrochloric acid or sulfuric acid for about several tens of hours to several days. The deamidation rate after acid treatment is about 0 to 2%.

Not only one kind of gelatin, but also gelatins with different materials and different physical properties, such as solubility, molecular weight, and isoelectric point, may be used in appropriate blends.

Although the properties of the gelatin vary according to the material and treatment method used, gelatin having any property can be used as a starting material for the crosslinked gelatin gel of the present invention as long as the gelatin does not include a pharmaceutically non-acceptable component.

The "hydrogel comprising a crosslinked gelatin gel" used in the present invention contains as a main component a gelatin gel formed by crosslinking gelatin with a chemical crosslinking agent or by heat treatment, ultraviolet irradiation, or electron beam irradiation.

The hydrogel comprising a crosslinked gelatin gel may contain, in addition to a crosslinked gelatin gel, dyes, proteins other than collagen, and/or salts, and like impurities in an amount within a pharmaceutically acceptable range.

The hydrogel comprising a crosslinked gelatin gel may contain the crosslinked gelatin gel in an amount of, for example, 95 to 100 w/v %, more preferably 99 to 100 w/v %, and most preferably 99.5 to 100 w/v %.

The chemical crosslinking agent for crosslinking the gelatin usable in the preparation of a crosslinked gelatin gel in the present invention is not particularly limited as long as it is not toxic to living bodies. For example, glutaraldehyde, water-soluble carbodiimides such as 1-ethyl-3-(3-dimethylaminopropyl)carbodiimide hydrochloride and 1-cyclohexyl-3-(2-morpholinoethyl)carbodiimide-metho-p-toluenesulfonate, bisepoxy compounds, formalin, and the like are preferable. Glutaraldehyde and 1-ethyl-3-(3-dimethylaminopropyl)carbodiimide hydrochloride are particularly preferable.

These crosslinking treatments may be used in combination. Alternatively, a crosslinked hydrogel may be prepared by physical cross-linking using salt bridge, electrostatic interaction, hydrogen bend, hydrophobic interaction, or the like. Using a chemical crosslinking agent is preferable from the viewpoint of the strength of crosslinking.

The degree of gelatin crosslinking can be suitably selected according to the rate (number of days) of decomposition of the crosslinked gelatin gel in the living body. The decomposition rate of the crosslinked gelatin gel can be measured, for example, by using the following method. 60 µl of PBS is added dropwise per mg of the crosslinked gelatin gel, on a dry weight basis, and allowed to stand at 37° C. for 1 hour or at 4° C. for 12 hours to 24 hours. After measuring the total weight of the crosslinked gelatin gel impregnated with PBS, the crosslinked gelatin gel is implanted subcutaneously into the back of several mice. Some of the mice are slaughtered every day or every 2 to 3 days to remove the implanted crosslinked gelatin gel and the wet weight of the crosslinked gelatin gel is measured. The point of time when the weight of the removed crosslinked gelatin gel has become approximately half of the wet weight of the PBS-impregnated crosslinked gelatin measured before implantation is defined as the half-life of the crosslinked gelatin gel (unit: number of days).

The crosslinked gelatin gel used in the present invention has a half-life of 5 to 25 days, preferably 8 to 22 days, more preferably 10 to 20 days, and even more preferably 14 to 19 days.

The degree of crosslinking of the crosslinked gelatin can be evaluated as water content. The water content can be determined according to, for example, the method disclosed in the report of Tabata, Y et al. (Tabata, Y et al., J. Controlled Release, 31: 189-199, 1994, Tabata, Y et al., Tissue Eng. 1999 (2):127-38). For example, 1 mg of a dry crosslinked gelatin gel is immersed in 1 to 3 ml of PBS (pH of 7.4) and incubated at 37° C. for about 24 hours with occasional agitation. After removing excess PBS, the wet weight of swollen crosslinked gelatin gel after impregnation with PBS (wet weight of the crosslinked gelatin gel after swelling) is measured.

The weight of absorbed water is calculated by subtracting the weight of the dry crosslinked gelating gel from the wet weight of the crosslinked gelatin gel after swelling. Specifically, the weight of absorbed water is calculated by the following formula.

Weight of absorbed water=(Wet weight of the crosslinked gelatin gel after swelling)−(Weight of the dry crosslinked gelatin gel)

The water content is calculated by dividing the weight of absorbed water by the wet weight of the crosslinked gelatin gel after swelling and multiplying the value by 100. Specifically, the water content is calculated by the following formula.

Water content (%)=(Weight of absorbed water/Wet weight of the crosslinked gelatin gel after swelling)×100

The crosslinked gelatin gel used in the present invention has a water content of 92 to 99.7%, preferably 93 to 98.5%, and more preferably 95 to 98%. The lower the water content of the crosslinked gelatin gel, the lower the biodecomposition rate of the crosslinked gelatin. The half-life of the crosslinked gelatin gel with a water content of 98.8% is about 6 to 8 days. The half-life of the crosslinked gelatin gel with a water content of 97.6% is about 10 to 14 days. The half-life of the cross linked gelatin gel with a water content of 96.9% is about 16 to 20 days.

A crosslinked gelatin gel having the above water content can be obtained, for example, by adjusting the concentrations of the gelatin and the crosslinking agent to the following ranges when the crosslinked gelatin gel is produced: a gelatin concentration of 1 to 20 wt. % and a crosslinking agent concentration of 0.01 to 1 wt. %. Further, a crosslinking agent with a desired water content can be obtained, for example, by appropriately adjusting the crosslinking reaction conditions to a temperature of 0 to 40° C. and a reaction time of 1 to 48 hours.

For example, when glutaraldehyde is used as a crosslinking agent, if glutaraldehyde is added to a 3 to 5 wt. % aqueous gelatin solution to a final concentration of 0.8 to 1.0 wt. %, and a crosslinking agent is performed at 4° C. for about 12 hours, a crosslinked gelatin gel with a water content of approximately 94% can be obtained. If glutaraldehyde is added to a 3 to 5 wt. % aqueous gelatin solution to a final concentration of 0.6 to 0.7 wt. % and a crosslinking reaction is performed under the same conditions as above, a crosslinked gelatin gel with a water content of approximately 97% can be obtained. If glutaraldehyde is added to a 3 to 5 wt. % aqueous gelatin solution to a final concentration of 0.1 to 0.4 wt. % and a crosslinking reaction is performed, a crosslinked gelatin gel with a water content of approximately 98% can be obtained.

When 1-ethyl-3-(3-dimethylaminopropyl)carbodiimide hydrochloride (EDC) is used as a crosslinking agent, if EDC is appropriately added to a 1 to 10 wt. % aqueous gelatin solution to a final concentration of 0.01 to 10 wt. % and a reaction is allowed to proceed at 4° C. for 24 hours, a crosslinked gelatin gel with a water content of 92 to 99.7% can be obtained.

Gelatin becomes insoluble in water when crosslinked. The term "water-insoluble" refers to the property of being able to be impregnated with a solution containing water and swelling but not dissolving in an aqueous solution containing water. The solubility of the crosslinked gelatin gel in water can be determined, for example, by adding 1 g of a dry powder crosslinking gelatin per 100 g of water at 60° C. and determining the gelatin gel to be water-soluble if the amount of gelatin dissolved after being allowed to stand for 1 hour is 0.1 g or more, and determining the gel to be water-insoluble if the amount of gelatin dissolved after being allowed to stand for 1 hour is less than 0.1 g.

The form of the crosslinked gelatin gel used in the present invention is not particularly limited. The crosslinked gelatin gel may be, for example, in the form of a cylinder, prism, sheet, disk, sphere, particle, granule, powder, paste, etc. when the sensitizer of the present invention is implanted into a tumor area, the crosslinked gelatin gel in the form of a cylinder, prism, sheet, or disk is preferable. The gel in the form of a sheet or disk is more preferable. When the sensitizer of the present invention is used in the form of formulation that is directly injected into a tumor area or intravascularly injected into a tumor area, the crosslinked gelatin gel in the form of a sphere, particle, granule, powder, or paste is preferable.

The crosslinked gelatin gel can be formed, for example, according to the methods disclosed in JP2004-203329A and JP2005-325075A.

Specifically, the crosslinked gelatin gel in the form of a cylinder, a prism, a sheet, or a disk can be prepared by mixing an aqueous gelatin solution with an aqueous solution of a crosslinking agent, then casting the mixture into a mold having a desired shape, and allowing a crosslinking reaction to proceed. The formed gelatin gel may be used as it is, or an aqueous solution of a crosslinking agent may be added after drying. To quench the crosslinking reaction, the reaction product is brought into contact with a low-molecular-weight substance having an amino group, such as ethanolamine or glycine, or an aqueous solution having a pH of 2.5 or less is added. The obtained crosslinked gelatin gel is washed with distilled water, ethanol, 2-propanol, acetone, or the like, and used to prepare a formulation.

The crosslinked gelatin gel in the form of a paste can be prepared by using a method similar to the method of preparing a crosslinked gelatin gel in the form of a cylinder, prisma, sheet, or disk.

The crosslinked gelatin gel in the form of a sphere, particle, or granule, can be obtained, for example, by the following method. An aqueous gelatin solution is placed in a device formed by attaching a stirring motor (e.g., Three-One Motor, manufactured by Shinto Scientific Co., Ltd., or EYELA mini D.C. Stirrer) and a stirring propeller of Teflon (trademark) to a three-necked round flask and fixing the flask equipped with the Stirring motor and the stirring propeller. After an oil such as olive oil is added and the resulting mixture is stirred at about 200 to 600 rpm to give a W/O emulsion, an aqueous solution of a crosslinking agent is added. Alternatively, after an aqueous gelatin solution pre-emulsified in olive oil (e.g., Advantec TME-21 vortex mixer or PT10-35 homogenizer polytron) is added dropwise to olive oil to give a fine particulate W/O emulsion, an aqueous solution of a crosslinking agent is added thereto. After a crosslinking reaction is allowed to proceed, the crosslinked gelatin gel is recovered by centrifugation, washed with acetone, ethyl acetate, etc., further washed with IPA, ethanol, etc., and dried. Subsequently, 100 mM glycine is added to an aqueous solution containing Tween 80, and the particles are suspended in the solution to quench the crosslinking reaction. The obtained crosslinked gelatin gel particles are washed successively with IPA, distilled water containing Tween 80, distilled water, etc., and used to prepare the formulation.

When the crosslinked gelatin gel particles are coagulated, for example, ultrasonication (preferably within about 1 minute under cooling) and the like may be applied.

By pre-emulsifying, crosslinked gelatin gel in the form of fine particles having an average particle size of 20 µm or less can be obtained.

The average particle size of the obtained crosslinked gelatin gel particles is 1 to 1,000 µm. Particles having a necessary size are appropriately sieved according to the object, and used. For local administration, particles having an average particle size of 10 to 150 µm are preferable. As used herein, the average particle size means an average diameter of the particles, which is assumed by passing the sieves. The water content of the obtained crosslinked gelatin gel particles is about 50 to 99 w/w %. and particles having a preferable water content can be appropriately prepared.

The crosslinked gelatin gel thus obtained can also be vacuum-dried or freeze-dried.

For freeze drying, for example, a crosslinked gelatin gel is placed in distilled water, frozen in liquid nitrogen for 30 minutes or mere at −80° C. for at least 1 hour and then dried in a freeze dryer for 1 to 3 days.

The dry crosslinked gelatin gel may be a commercially available product, such as MetJel (registered trademark) manufactured by MedGel Corporation.

The sensitizer of the present invention is a composition comprising a combination of hydrogen peroxide (herein also referred to as "component (a)") and a hydrogel comprising a crosslinked gelatin gel (herein also referred to as "component (b)").

The phrase "comprising a combination" as used herein inclusively means all the following cases for the sensitizer of the present invention:
(i) the sensitizer contains both component (a) and component (b) from the beginning (a combination drug), i.e., component (b) is impregnated with component (a), or (i)' component (b) is impregnated with component (a) and the resulting product is floated or suspended in physiological saline, etc.;
(ii) a formulation containing component (a) and a formulation containing component (b) are separately packaged and sold as a combination (a kit); or
(iii) a formulation containing component (a) and a formulation containing component (b) are separately packaged and are in separate market distribution channels, and are combined when used. That is, "the sensitizer comprising a combination" as used herein means that the sensitizer that is ultimately used (herein also referred to as "final formulation") contains both component (a) and component (b), and the form during the distribution stage, including sale, is not particularly limited.

The phrase "comprising a combination of component (a) and component (b)" inclusively means "containing component (a) and component (b)," "substantially consisting of component (a) and component (b)," and "consisting of component (a) and component (b)."

The proportion of hydrogen peroxide contained as component (a) in the sensitizer of the present invention is not limited, and can be suitably selected from the range that the amount of hydrogen peroxide in the final formulation is in the range of 0.01 to 3.5 w/v %. The amount is preferably in the range of 0.1 to 3 w/v %, and more preferably 0.5 to 2 w/v %.

The proportion of the hydrogel comprising a crosslinked gelatin gen to hydrogen peroxide is not particularly limited, and can be suitably selected from the range that the amount of the hydrogel comprising a crosslinked gelatin gel per 300 µg of hydrogen peroxide (10 µl of a 3 w/v % aqueous hydrogen peroxide solution) is in the range of 0.1 to 100 mg (dry weight), preferably 0.5 to 50 mg (dry weight), and more preferably 0.8 to 10 mg (dry weight).

The proportion of the hydrogel comprising a crosslinked gelatin gel in the sensitizer (final formulation) of the present invention is not particularly limited, and can be suitably selected from the range of 0.05 to 20 w/v %, preferably 0.1% to 10 w/v %, and more preferably 0.5 to 5 w/ %. The weight (w) of the hydrogel comprising a crosslinked gelatin gel is on a dry weight basis.

The method for impregnating the hydrogel comprising a crosslinked gelatin gel with an aqueous hydrogen peroxide solution comprises weighing a required amount of the hydrogel comprising a dry crosslinked gelatin gel in the form of a cylinder, prism, sheet, disk, sphere, particle, granule, or powder, and adding the aqueous hydrogen peroxide solution dropwise to the hydrogel comprising a crosslinked gelatin gel using a pipette, etc., in an amount to achieve the proportion mentioned above, followed by incubation, for example, at 30 to 37° C. for about 15 minutes to about 2 hours, or at 2 to 8° C. for about 12 to 24 hours, and preferably at 37° C. for about 1 hour, or at 4° C. for about 12 to 18 hours.

To fix the qualities as a sensitizer, the aqueous hydrogen peroxide solution is preferably added dropwise in a volume such that the sensitizer can be impregnated with all the aqueous hydrogen peroxide solution added dropwise.

The product obtained by impregnating the hydrogel comprising a crosslinked gelatin gel with the aqueous hydrogen peroxide solution by using the above method may be used as a sensitizer as is or after being further floated or suspended in pharmaceutically acceptable physiological saline or phosphate buffer (such as sodium chloride, disodium hydrogen phosphate, and sodium dihydrogen phosphate). Even when the hydrogel comprising a crosslinked gelatin gel is impregnated with an aqueous hydrogen peroxide solution and further floated or suspended in physiological saline or the like, the final contents of the hydrogen peroxide and the hydrogel comprising a crosslinked gelatin gel can be adjusted to the ranges mentioned above.

The liquid properties of the sensitizer of the invention are not particularly limited as long as it is compatible with the human body. The sensitizer is preferably adjusted to a pH of 6 to 8.5, and more preferably a pH of 6.5 to 8.0.

I-2. Method for Applying the Sensitizer

The sensitizer of the present invention is in the form of a liquid (including a solution, an emulsion, and a suspension), a gel, or an elastic solid. As long as the sensitizer is in such a form, the mode of use (usage) is not particularly limited. For example, when the sensitizer of the present invention is a liquid or gel external formulation, the sensitizer can be locally administered to the tumor area, for example, by the following methods: methods of directly spraying, applying, or attaching the sensitizer onto the tumor area during the irradiation with radiation in the radiotherapy or during administration of an anti-cancer agent in anti-cancer chemotherapy, and methods of impregnating sterile cotton or gauze with the sensitizer and applying the impregnated sterile cotton or gauze to the tumor area to be irradiated with radiation during the irradiation.

When the sensitizer of the present invention is a liquid or gel injection, the injection can be directly injected into the tumor area to be treated, preferably intratumorally injected, using a syringe or the like, or indirectly injected via an angiography catheter into the tumor area, before, simultaneously with, or after the irradiation with radiation or the administration of an anti-cancer agent.

Specifically, the sensitizer is preferably injected by using a syringe with a needle of about 21 gauge while observing the state of permeation of the sensitizer into the tissue under ultrasonographic guidance. In this case, the sensitizer can be distributed widely to the tissue under ultrasonographic guidance by modifying the depth and direction of the injection needle. The sensitizer may be injected into the tumor area via the vasa vasorum of the tumor. The dose of the sensitizer in the present invention administered to the tumor area varies depending on the size of the tumor and the administration method. For example, when the sensitizer is injected into the tumor area, the dose (injection amount) may be typically about 1 to 5 ml, and preferably about 3 ml.

When the sensitizer of the present invention is in the form of an elastic solid, the sensitizer may be implanted by incising the tumor area or the area after resection of the tumor using a scalpel or the like.

In another embodiment, the dose of the sensitizer in the present invention can also be set according to the tumor volume. The tumor volume (V) can be calculated, for example, by measuring the minor axis (W) and major axis (L) of the tumor using a Vernier caliper, and substituting the obtained values into the following equation: $V=(W^2 \times L)/2$. The lower limit of the dose of the sensitizer administered to mice in accordance with the tumor volume is 0.1, 0.2, 0.3, 0.4, or 0.5 mg, on a dry weight basis of the crosslinked gelatin gel contained in the final formulation, per 200 $mm^3$ of the tumor volume. The upper limit of the dose of the sensitizer is 10, 5, 3, 2, or 1 mg, on a dry weight basis of the crosslinked gelatin gel contained in the final formulation, per 200 $mm^3$ of the tumor volume. Any combination of the upper limit and lower limit may be used. The lower limit is preferably 0.1 mg, and the upper limit is preferably 1 mg.

The dose administered to humans can be set in accordance with the dose administered to mice. If necessary, the sensitizer may be administered to humans at 5 to 10 times the dose administered to mice. The lower limit of the dose of the sensitizer administered to a human in accordance with the tumor volume may be, for example, 0.5, 1, 1.5, 2, or 2.5 mg, on a dry weight basis of the crosslinked gelatin gel contained in the final formulation, per 200 $mm^3$ of the tumor volume. The upper limit of the dose of the sensitizer may be, for example, 5, 8, 10, 15, or 20 mg, on a dry weight basis of the crosslinked gelatin gel contained in the final formulation, per 200 $mm^3$ of the tumor volume. Any combination of the upper limit and lower limit may be used. The lower limit is preferably 0.5 mg, and the upper limit is preferably 5 or 10 mg.

The sensitizer of the present invention is preferably in the form of an injection (a radiotherapy sensitizer injection or anti-cancer chemotherapy sensitizer injection). The injection can be obtained by preparing an aqueous solution using water for injection (distilled water for injection, sterile water for injection, etc.), an isotonizing agent, a pH control agent, a buffer solution, and the like, adding component (a) and component (b) to the resulting aqueous solution in amounts to achieve the proportions mentioned above, placing the resulting mixture in a container and sealing the container, followed by sterilization using high-pressure steam sterilization, hot water immersion sterilization, or the like. Alternatively, the injection (a preparation prepared just before use) can be obtained by mixing a formulation containing component (a) and a formulation containing component (b) at the time of use, optionally using water for injection (distilled water for injection, sterile water for injection, etc.).

Examples of usable isotonizing agents include sodium, chloride, glycerin, glucose, polyethylene glycol, propylene glycol, D-mannitol, fructose, xylitol, sodium dihydrogen phosphate, and sodium phosphate. Sodium chloride is preferably used. Examples of pH control agents include hydrochloric acid and sodium, hydroxide. As described above, the injection is adjusted to a pH range of 6 to 8.5, and preferably to a pH range of 6.8 to 7.8. Examples of buffers that can be used for maintaining the pH include phosphate buffers, Tris buffers, and acetate buffers. A phosphate buffer is preferably used.

I-3. Radiotherapy Using the Sensitizer

As described above, in radiotherapy, the sensitizer of the invention is applied to a tumor area to be irradiated with radiation before the irradiation. The sensitizer can be preferably used in radiotherapy of tumors that are resistant to radiotherapy.

Examples of tumors that are radioresistant include tumors that have many hypoxic tumor cells and tumors that have large amounts of antioxidative enzymes. The biggest problem with linear-accelerator-based cancer radiotherapy, which is commonly used currently, is the presence of radioresistant cancer cells. The radioresistant tumor tissues are mostly in hypoxic regions and are resistant to radiotherapy. The radiation resistance of these cells is considered to be attributable to the following: in a hypoxic state, DNA damage, etc., of the cells induced by radiation are not fixed by oxygen; furthermore, reactive oxygen species produced in tumor cells by radiation are eliminated by anti-oxidative enzymes, thus making it difficult to induce apoptosis. Specific examples of radioresistant tumors include malignant melanomas, malignant glioblastomas, and various types of sarcomas such as osteosarcomas, as well as nearly all types of locally advanced cancers that have grown to several centimeters or more.

Radiotherapy using the sensitizer of the invention can be performed by first applying the sensitizer to the area of the tumor to be irradiated with radiation, and then irradiating the affected part with X-rays or electron beams preferably using a linear accelerator. The x-ray irradiation conditions differ depending on how far the tumor has advanced, its size, and the like. One dose of radiation may typically be 1.5 to 3 Gy, preferably about 2 Gy, and the irradiation may be performed 2 to 5 times a week, and more preferably about 4 or 5 times a week, over a period of 1 to 5 weeks, with a total dose of 20 to 70 Gy, preferably about 40 to 70 Gy, and more preferably about 50 to 60 Gy. The electron beam conditions also differ depending on how far the tumor has advanced, its size, and the like. One dose of radiation may typically 2 to 5 Gy, preferably about 4 Gy, and the irradiation may be performed 1 to 5 times a week, and more preferably about 2 or 3 times a week, over a period of 1 to 5 weeks, to a total dose of 30 to 70 Gy, and preferably about 40 to 60 Gy.

The sensitizer of the invention may be administered simultaneously with or before the first irradiation with radiation. More specifically, the first administration of the sensitizer of the present invention is preferably performed during the period from 3 days before the start of the irradiation with radiation until the start of the irradiation, more preferably during the period from 2 days before the start of the irradiation with radiation until the start of the irradiation, and even more preferably 1 day before the start of the irradiation until the start of the irradiation, or immediately before the irradiation with radiation. The second or later administration of the sensitizer can be performed 5 to 14 days after the previous administration of the sensitizer, and more preferably 7 to 10 days after the previous administration.

For example, when the irradiation with radiation is performed 4 to 5 times a week for 4 weeks, if the irradiation is stated on Monday, the sensitizer of the present invention may be administered before the irradiation every Monday.

The frequency of administration of the sensitizer of the present invention can be increased or decreased according to the therapeutic effects on tumors.

When radiotherapy is performed in advance and the effect of irradiation with radiation is not obtained, use of the sensitizer of the present invention may be started after the start of radiotherapy.

When radiotherapy is started after a surgical operation, radiotherapy cay be started in advance and use of the sensitizer of the present invention may be started, for example, 5 to 14 days, and more preferably 6 to 8 days, after the start of irradiation with radiation.

For example, when radiotherapy is performed after breast conservative surgery, the whole breast is irradiated with a dose of 50 Gy (2 Gy×5 times/(week)). When tumor cells are observed at the surgical margin during the surgery, for example, the tumor cells can be boost-irradiated with an electron beam to a total dose of 10 Gy (2 Gy×5 times). In another embodiment, for example, the whole breast irradiated to 44 Gy (2.75 Gy×16 times), and boost-irradiated to 9 Gy (3 Gy×3 times). The sensitizer of the present invention can be locally administered to the tumor area, for example, 1 week after the start of the irradiation. The frequency of administration of the sensitizer may be, for example, 1 to 4 times.

I-4. Anti-Cancer Chemotherapy Using the Sensitizer

The sensitizer of the invention may be used on the tumor area to be treated, before therapy with an anti-cancer agent. The sensitizer can be preferably used on tumors that are resistant to therapy with an anti-cancer agent or that are relatively large. For example, many solid tumors, such as stomach cancer, non-small-cell lung cancer, colorectal and rectal cancer, liver cancer, pancreatic cancer, uterine cancer, and esophageal cancer, are resistant to anti-cancer agents. With respect to such solid tumors, nearly all locally advanced solid tumors tend to be resistant to anti-cancer agents.

The sensitizer of the present invention can be administered simultaneously with, or before the first administration of the anti-cancer agent. More specifically, the first administration of the sensitizer of the present invention is preferably perforated during the period from 3 days before the start of the administration of the anti-cancer agent until the start of the administration, more preferably during the period from 2 days before the start of the administration of the anti-cancer agent until the start of the administration, and even more preferably 1 day before the start of the administration of the anti-cancer agent until the start of the administration, or immediately before the start of the administration of the anti-cancer agent. The second or later administration of the sensitizer can be performed 5 to 14 days after the previous administration of the sensitizer, and more preferably 7 to 10 days after the previous administration.

For example, when the anti-cancer agent is administered once to five times per week for 4 weeks, and if the administration of the anti-cancer agent is started on Monday, the sensitizer of the invention may be administered before the start of the administration of the anti-cancer agent every Monday.

The frequency of administration of the sensitizer of the present invention can be increased or decreased according to the therapeutic effects on tumors.

When an anti-cancer agent is administered in advance and the effect of the anti-cancer agent is not obtained, use of the sensitizer of the present invention may be started after the start of the administration of the anti-cancer agent.

Examples of anti-cancer agents (carcinostatic agents) used in the present invention include alkylating agents such as cyclophosphamide, ifosfamide, busulfan, melphalan, bendamustine hydrochloride, nimustine hydrochloride, zanimustine, dacarbazine, procarbazine hydrochloride, and temozolomide; antimetabolites such as methotrexate, pemetrexed sodium, fluorouracil, doxifluridine, capecitabine, tegafur, cytarabine, cytarabine ocfosfate hydrate, enocitabine, gemcitabine hydrochloride, mercaptopurine hydrate, fludarabine phosphate, nelarabine, pentostatin, cladribine, levofolinate calcium, calcium folinate, hydroxycarbamide, L-asparaginase, and azacitidine; antitumor antibiotics such as doxorubicin hydrochloride, daunorubicin hydrochloride, pirarubicin, epirubicin hydrochloride, idarubicin hydrochloride, aclarubicin hydrochloride, amrubicin hydrochloride, mitoxantrone hydrochloride, mitomycin C, actinomycin D, bleomycin, peplomycin sulfate, and zinostatin stimalamer; microtubule inhibitors such as vincristine sulfate, vinblastine sulfate, vindesine sulfate, vinorelbine tartrate, paclitaxel, docetaxel hydrate, and eribulin mesylate; hormonal agents such as anastrozole, exemestane, letrozole, tamoxifen citrate, toremifene citrate, fulvestrant, flutamide, bicalutamide, medroxyprogesterone acetate, estramustine phosphate sodium hydrate, and leuprolide acetate; platinum drugs such as cisplatin, miriplatin hydrate, carboplatin, nedaplatin, and oxaliplatin; topoisomerase I inhibitors such as irinotecan hydrochloride hydrate and nogitecan hydrochloride; topoisomerase II inhibitors such as etoposide and sobuzoxane; cytokines such as interferon γ-1a, teceleukin, and celmoleukin; antibody drugs such as trastuzumab, rituximab, gemtuzumab ozogamicine, bevacizumab, and cetuximab; radioimmunotherapeutic agents such as ibritumomab tiuxetan; molecular target drugs such as gefitinib, imatinib mesylate, bortezomib, erlotinib hydrochloride, sorafenib tosylate, sunitinib malate, thalidomide, nilotinib hydrochloride hydrate, dasatinib hydrate, lapatinib tosylate hydrate, everolimus, lenalidcmide hydrate, dexamethasone, temsirolimus, vorinostat, tretinoin, and tamibarotene; non-specific immune stimulants such as OK-432, dry BCG, Coriolus versicolor polysaccharide formulation, lentinan, and ubenimex; and anti-cancer agents such as aceglatone, porfimer sodium, talaporfin sodium, ethanol, and arsenic trioxide.

Examples of more preferable anti-cancer agents include anthracycline anti-cancer agents such as doxorubicin hydrochloride, daunorubicin hydrochloride, pirarubicin, epirubicin hydrochloride, idarubicin hydrochloride, aclarubicin hydrochloride, anrubicin hydrochloride, and mitoxantrone hydrochloride; platinum anti-cancer agents such as cisplatin, miriplatin hydrate, carboplatin, nedaplatin, and oxaliplatin; and pyrimidine antimetabolite-based anti-cancer agents such as fluorouracil, doxifluridine, capecitabine, tegafur, cytarabine, cytarabine ocfosfate hydrate, enocitabine, and gemcitabine hydrochloride.

These anti-cancer agents or carcinostatic agents can be used singly or in a combination of two or more.

The method of administering the anti-cancer agent can be suitably selected from known administration methods basically according to each anti-cancer agent. The anti-cancer agent can be administered according to the administration method, dose, and method of application described in instructions for using each anti-cancer agent. When combined use of the anti-cancer agent with the sensitizer can promote reduction in size of a tumor, the dosage and frequency of administration of the anti-cancer agent can be reduced.

II. Method for Treating Tumor

Another embodiment of the present invention provides a method of treating a tumor comprising (1) locally administering a sensitizer comprising (a) hydrogen peroxide and (b) a hydrogel comprising a crosslinked gelatin gel to a tumor area, and (2) irradiating the tumor area with radiation or administering an anti-cancer agent to a patient suffering from the tumor.

The composition of the sensitizer used in the method of treating a tumor, the method for applying the sensitizer, and methods of performing radiotherapy or anti-cancer chemotherapy are in accordance with those described in "I. Sensitizer for Enhancing Therapeutic Effect of Radiation or Anti-cancer agent on Tumor."

III. Composition for Treating Tumor Using Radiation or Anti-Cancer Agent

Another embodiment of the present invention is a composition for treating a tumor by using radiation or an anti-cancer agent, the composition comprising a combination of (a) hydrogen peroxide and (b) a hydrogel comprising a crosslinked gelatin gel, and the composition being locally administered to a tumor area.

This composition is the same as the sensitizer described in "I. Sensitizer for Enhancing Therapeutic Effect of Radiation and Anti-cancer agent on Tumor" and can be produced by using the same method as the method for producing the sensitizer. The method for applying the composition is also the same as for the sensitizer.

IV. Use in Manufacture of the Sensitizer for Increasing the Sensitivity to the Therapeutic Effect of Radiation and Anti-Cancer Agent on Tumor Another embodiment of the present invention is use of a composition for local administration to a turner area in the manufacture of a sensitizer for enhancing a therapeutic effect of radiation or an anti-cancer agent on a tumor, the composition comprising a combination of the following components (a) and (b):

(a) hydrogen peroxide; and
(b) a hydrogel comprising a crosslinked gelatin gel.

The above (a) hydrogen peroxide and (b) hydrogel comprising a crosslinked gelatin gel according to this embodiment may be the same as those described in "I. Sensitizer for Enhancing Therapeutic Effect of Radiation or Anti-cancer agent on Tumor." The method for producing the sensitizer and the method for applying the sensitizer may also be in accordance with those described in "I. Sensitizer for Enhancing Therapeutic Effect of Radiation or Anti-cancer agent on Tumor."

EXAMPLES

The present invention is described below in more detail with reference to Examples and Formulation Examples. However, the present invention is not limited by the Examples, etc. In this specification, % means w/v % unless otherwise specified.

The animal experiments described in the Examples below were performed with the approval of Kochi University Institutional Animal Care and Use Committee in the Institute for Laboratory Animal Research in the Department of Biofunctional Materials, Science Research Center, of Kochi University.

Formulation Example 1 of Sensitizer

10 μl of an aqueous hydrogen peroxide solution (about 3 w/v %) was directly added dropwise per mg of MedGel (registered trademark) particles (PI5-95MS: a crosslinked gelatin hydrogel prepared from gelatin with an isoelectric point of 4.8 to 5.0), and was tapped lightly. The mixture was allowed to stand at 37° C. for 1 hour to fully impregnate MedGel with the aqueous hydrogen peroxide solution, and the MedGel impregnated with the aqueous hydrogen peroxide solution was floated on 50 μl of PBS. In this case, the final concentration of hydrogen peroxide was about 0.5 w/v %, and the final concentration of MedGel was 1.67 w/v %.

The resulting sensitizer contained MedGel (crosslinked gelatin hydrogel) in an amount of 2 mg, on a dry weight basis, per 100 μl of the sensitizer.

Formulation Example 2 of Sensitizer

10 μl of an aqueous hydrogen peroxide solution (about 0.5 w/v %) was directly added dropwise per mg of MedGel (registered trademark) (PM-SF01: a crosslinked gelatin hydrogel prepared from gelatin with an isoelectric point of 8.0 to 9.0). The mixture was then allowed to stand at 37° C. for 1 hour to fully impregnate MedGel with the aqueous hydrogen peroxide solution (about 0.5 w/v %). The aqueous hydrogen peroxide (about 0.5 w/v %) was prepared by diluting an aqueous hydrogen peroxide solution (about 3 w/v %) 6-fold with PBS, and used. In this case, the final concentration of hydrogen peroxide was about 0.5 w/v %, and the final concentration of MedGel was 1.67 w/v %.

Comparative Example 1

Hydrogen peroxide was diluted with PBS to a final concentration of 0.5 w/v %.

Comparative Example 2

Immediately before use, 0.5 ml of an about 3 w/v % aqueous hydrogen peroxide solution was added to a syringe containing 25 mg of a hyaluronic acid formulation containing sodium hyalurotate in a concentration of 1 w/v % (trade name ARTZ Dispo (registered trademark), produced by Seikagaku Corporation, containing 25 mg of sodium hyaluronate per syringe (2.5 ml), and further containing 2.5 mg of L-methionine, sodium chloride, disodium hydrogen phosphate, crystalline sodium dihydrogenphosphate, and an isotonizing agent; colorless transparent viscous aqueous liquid, pH; 6.8 to 7.8, osmotic pressure ratio: 1.0 to 1.2 (ratio to the physiological saline), weight average molecular weight: 600,000 to 1,200,000) and the resulting mixture was mixed well to prepare a radiation sensitizer or anti-cancer chemotherapy sensitizer according to the present invention. The concentration of sodium hyaluronate and the concentration of hydrogen peroxide in this sensitizer were 0.83 w/v % and about 0.5 w/v %, respectively.

Example 1

Comparison Between the Hydrogel Method and the KORTUC Method in Effect

1. Method

Using 7-week old C3H/He female mice as experimental animals, an experiment was performed in an animal experimentation facility. The mice were kept in a facility that was maintained at room temperature and at a constant humidity and in which food and water were freely available.

SCCVII tumor cells ($1.0\times10^5$ cells/animal) were implanted subcutaneously into the right lower thigh of the mice. The mice were grouped as follows:

Group 1: Control group (receiving the sensitizer of Comparative Example 1)
Group 2: KORTUC group (receiving the sensitizer of Comparative Example 2)
Group 3: MedGel group (receiving the sensitizer of Formulation Example 1)

Figure 1:
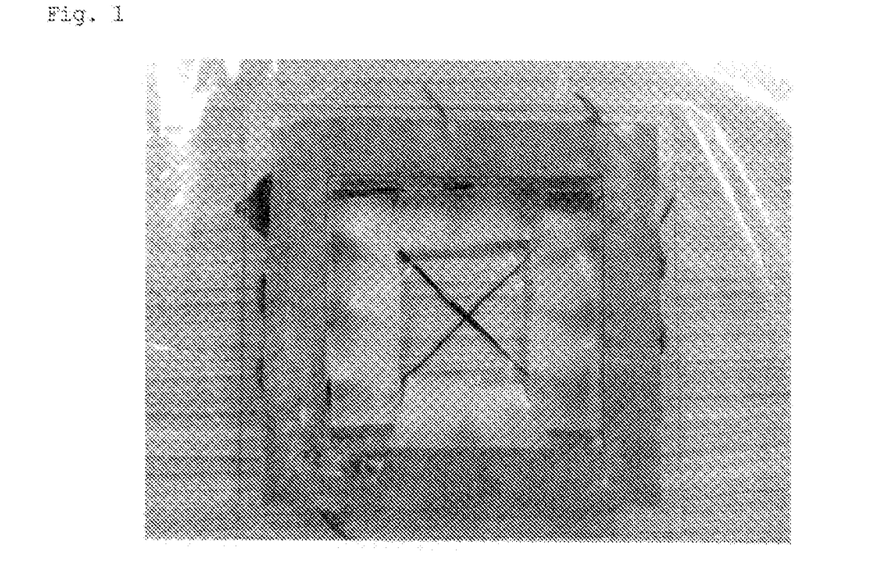
FIG. 1 shows a bolus and a device to which each mouse was secured when the mouse was irradiated with radiation.

At the stage of a tumor diameter of about 1 cm, the sensitizers obtained in Comparative Example 1, Comparative Example 2, and Formulation Example 1 were injected into the tumor areas. For the injection, an insulin syringe (with a 26-gauge needle) was used, and each sensitizer was injected in an amount of 200 μl. 72 hours after the administration of the sensitizer, electron beams with an energy of 6 MeV were irradiated with 30 Gy using a linear accelerator (EXL-20TP, produced by Mitsubishi Electric, Tokyo). When irradiated, the mice were anesthetized and irradiated using a mouse-immobilizing device. (FIG. 1). This device is for locally irradiating a leg portion in mice end protecting the whole body other than the leg portion having a tumor by using a copper plate with a thickness of 4.5 mm.

With the observation period set to 60 days, changes in tumor volume and survival rate were then checked. The tumor volume was observed using a Vernier caliper.

The tumor volume (V) was obtained by measuring the minor axis (W) and major axis (L) of the tumor with a Vernier caliper and calculating the tumor volume by the following formula: $V=(W^2\times L)/2$.

2. Results

Figure 2:
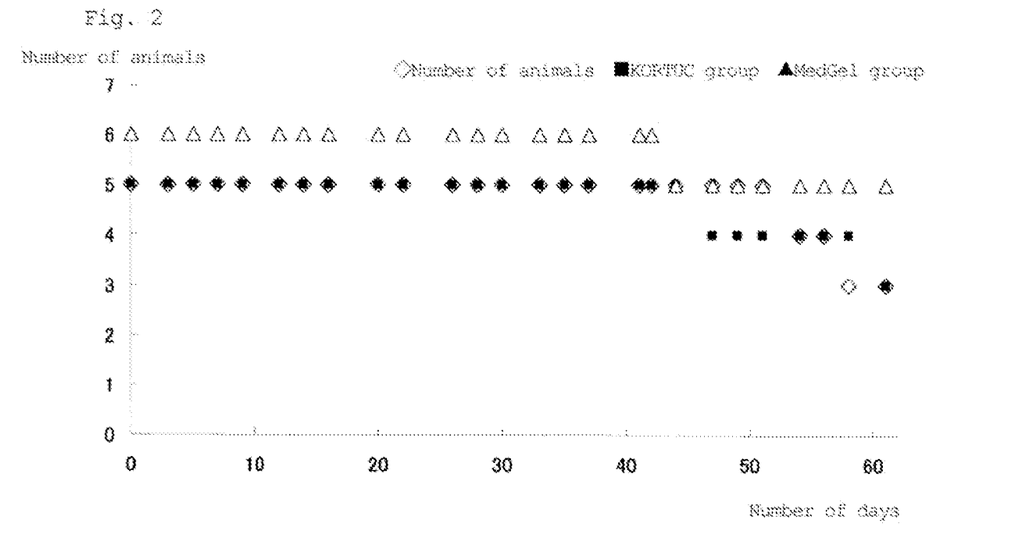
FIG. 2 shows the survival curve of each group after irradiation with radiation (◇: control group, ■: KORTUC-administered group, Δ: MedGel-administered group). Specifically, after tuner cells were implanted in mice, PBS+ hydrogen peroxide (control), hyaluronic acid+hydrogen peroxide (KORTUC), or MedGel+hydrogen peroxide (Med-Gel) were administered to the nice, and 72 hours after the administration, the mice were irradiated with radiation.

As shown in FIG. 2, mice in the MedGel group had the highest survival rate, and their survival rate after 60 days was 80%. The control group had a survival rate of 60%. The KORTUC group had a survival rate of 50%. If one animal that died from anesthesia when irradiated is excluded, the survival rate of the KORTUC group is 60%, which is the same as the survival rate of the control group.

The irradiation in this experiment was performed 72 hours after locally injecting each drug into the tumor area. The conventional KORTUC can maintain a partial pressure of oxygen in tumor tissue for 24 hours. Therefore, it is thought that in this experiment, the partial pressure of oxygen in tumor tissue had already decreased in the KORTUC group before the irradiation with radiation, and sufficient therapeutic effects were therefore not obtained.

The results suggest that the hydrogel comprising a crosslinked gelatin gel according to the present invention can maintain the partial pressure of oxygen in tumor tissue not only immediately after the administration of sensitizers but also 72 hours after the administration.

Figure 3:
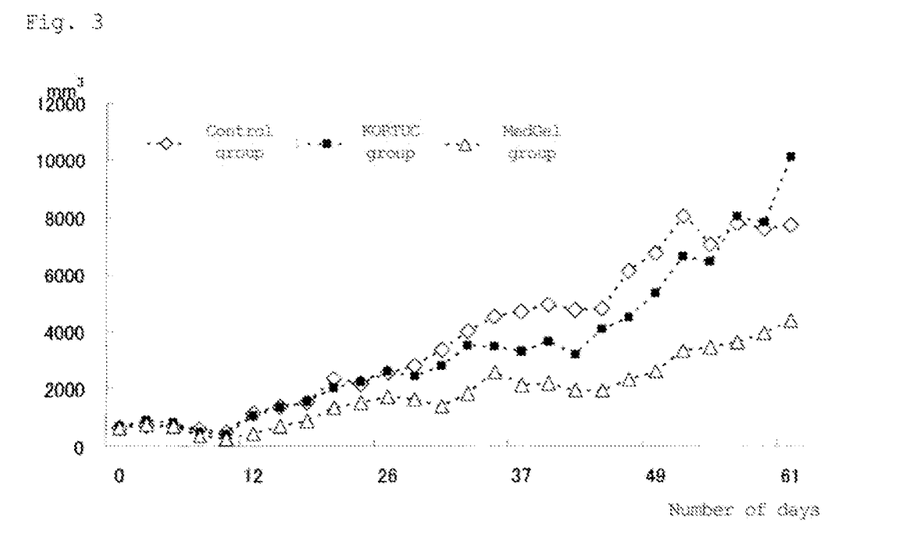
FIG. 3 shows the tumor volume curve of each group after irradiation with radiation (◇: control group, ■: KORTUC-administered group, Δ: MedGel-administered group.) Specifically, after tumor cells were implanted in mice, PBS+ hydrogen peroxide (control), hyaluronic acid+hydrogen peroxide (KORTUC), or MedGel+hydrogen peroxide (Med-Gel) were administered to the mice, and 72 hours after the administration, the mice were irradiated with radiation.
Figure 4:
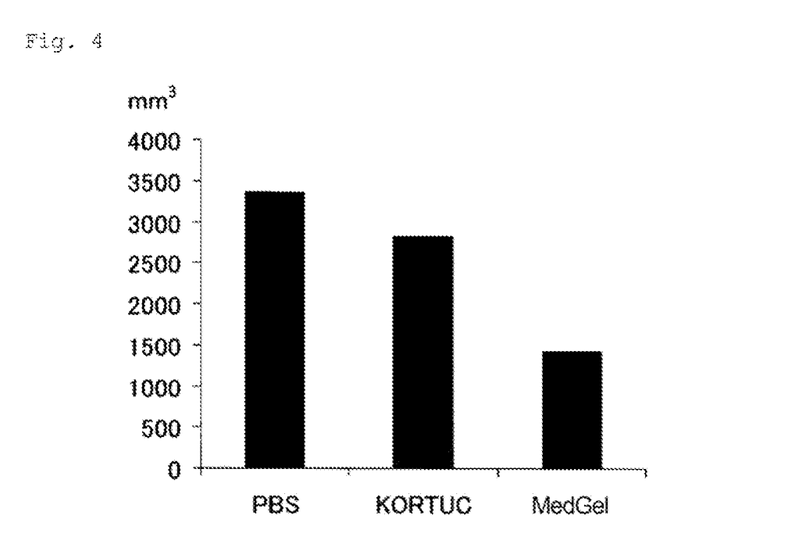
FIG. 4 shows a comparison in tumor volume on day 30 from the start of measurement in the graphs shown in FIG. 3 (from left to right, the control group, KORTUC-administered group, and MedGel-administered group).

With respect to changes in tumor volume, the tumor growth rate was mostly greatly inhibited in the MedGel group (FIG. 3). In the measurement on day 30 from the start of the measurement, the average tumor volume in the MedGel group was equal to half or less than half the volume in the other groups (FIG. 4). The MedGel group had two mice in which tumors were determined to have disappeared. One of the mice was determined to be tumor-free on day 5 from the start of the measurement. Another was determined to be tumor-free on day 20. However, the mouse which was determined to be tumor-free on day 20 actually had contracture at the joint and no tendency of tumor growth was observed; therefore, the mouse was determined to have not a tumor but a contracture at the joint. However, since tendency for tumor growth was observed later, the measurement was started at that point in time. The control group also had a mouse in which a tumor was determined to have disappeared. However, since tendency for tumor growth was observed again, it was determined to be a tumor and the measurement was started at that point in time.

The results of this experiment suggest that the hydrogel comprising the crosslinked gelatin gel of the present invention is the most effective substrate in terms of maintaining oxygen partial pressure in tumor tissue, compared to the KORTUC group. The MedGel group had the highest survival rate, and disappearance of tumors was visually observed in some of the mice, and a therapeutic effect of almost complete response was observed. These results were obtained presumably because using a combination of hydrogen peroxide and a hydrogel comprising a crosslinked gelatin gel as a sensitizer can increase the sensitivity to radiotherapy and thus enhance tumor inhibitory effects.

Example 2: The Dependent Change in the Form of MedGel

Figure 5:
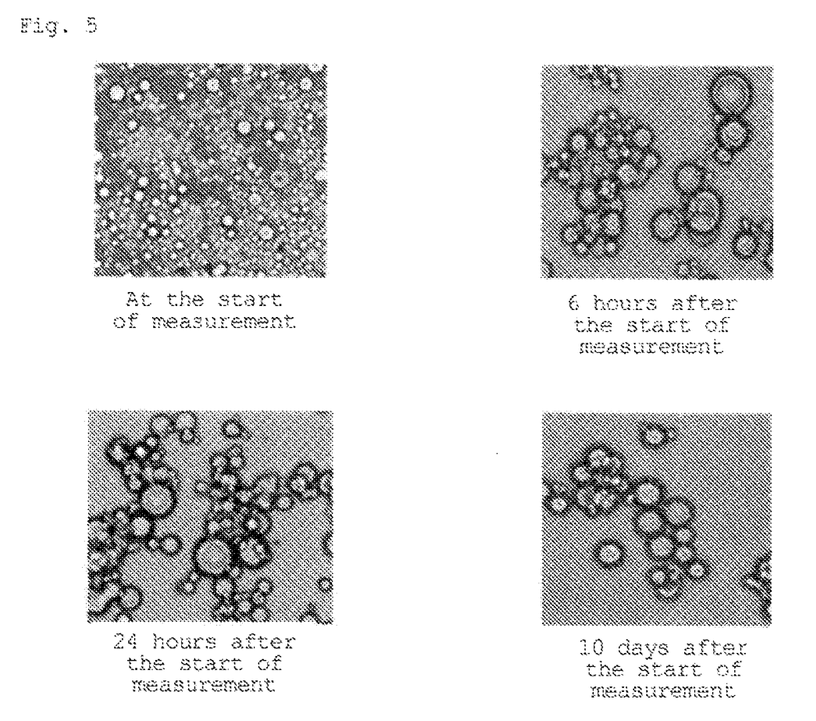
FIG. 5 shows time-dependent changes of MedGel particles in oxydol during the period up to 10 days later.

MedGel was mixed with an aqueous hydrogen peroxide solution (oxydol) according to Formulation Example 1, and time-dependent changes in the form of MedGel were observed (FIG. 5).

Even after 10 days, MedGel particles were not dissolved and MedGel maintained its form.

This result suggests that release of hydrogen peroxide by MedGel continues during radiotherapy.

Example 3: Effect on Tumor Volume of Irradiation with Radiation Performed 43 Hours After Administration of the Sensitizer to Tumor 1. Method SCCVII tumor cells ($1.0\times10^5$ cells/animal) were implanted subcutaneously into the lower-right thigh of the mice in the same manner as in the "1. Method" section of Example 1. The mice were grouped as follows:

Group 1: Control group (receiving no sensitizer)
Group 2: KORTUC group (receiving 100 μl of the sensitizer of Comparative Example 2)
Group 3: PI5-100 group (receiving the sensitizer of Formulation Example 1 in an amount of 2 mg, on a dry weight basis of MedGel)
Group 4: PI5-30 group (receiving the sensitizer of Formulation Example 1 in an amount of 0.6 mg, on a dry weight basis of MedGel)
Group 5: PI9-2 group (receiving the sensitizer of Formulation Example 2 in an amount of 2 mg, on a dry weight basis of MedGel)
Group 6: PI9-0.6 group (receiving the sensitizer of Formulation Example 2 in an amount of 0.6 mg, on a dry weight basis of MedGel)

At the stage of a tumor volume of about 200 to 250 mg, 100 μl of the sensitizer of Comparative Example 2, 100 μl of the sensitizer of Formulation Example 1 (in an amount of 2 mg, on a dry weight basis of MedGel), or 30 μl of the sensitizer of Formulation Example 1 (in an amount of 0.6 mg, on a dry weight basis of MedGel) was injected into tumors. Because the sensitizer of Formulation Example 2 was in the form of an elastic solid, the tumor area was incised and the sensitizer was implanted in an amount of 2 or 0.6 mg, on a dry weight basis of MedGel (crosslinked gelatin gel), per about 200 to 250 mg of the tumor volume.

Forty-eight hours after the administration of the sensitizer, tumor cells were irradiated with radiation under the same condition as in the "1. Method" section of Example 1, and the tumor volume on day 37 from the administration of the sensitizer (on day 35 from the irradiation) was measured.

2. Results

Figure 6:
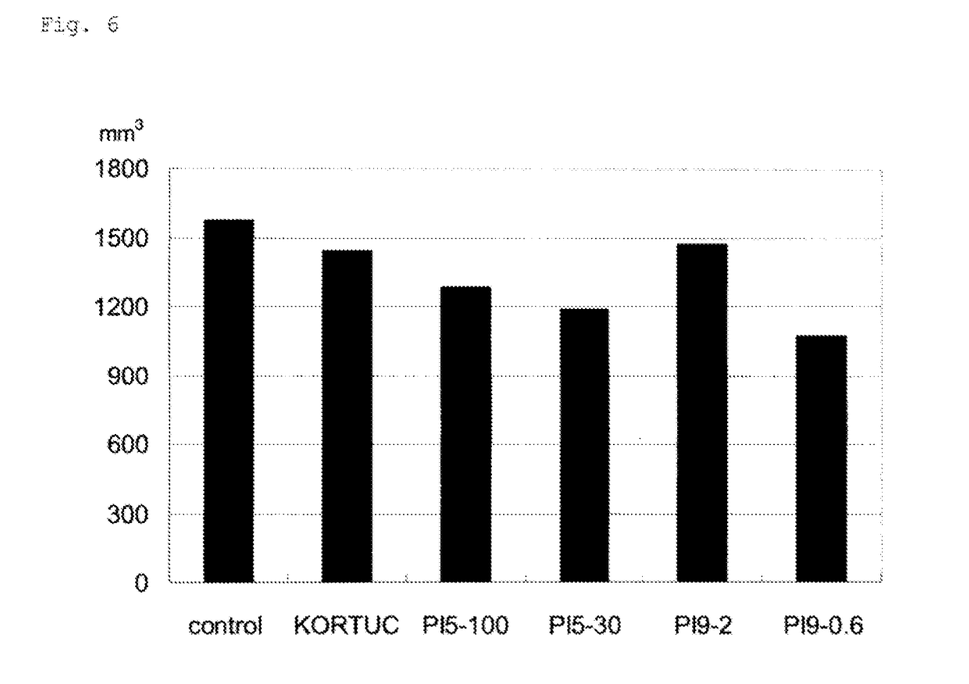

As shown in FIG. 6, no substantial difference was observed in tumor volume among the KORTUC group (KORTUC), PI9-2 group (PI9-2), and the control group (control). In contrast, a tumor volume increase was inhibited in the PI5-100 group (PI5-100), PI5-30 group (PI5-30), and PI9-0.6 group (PI9-0.5), compared to the KORTUC group. In particular, in the PI5-30 group and PI9-0.6 group, this inhibition effect was great. These results suggest that the hydrogel comprising a crosslinked gelatin gel is preferably locally administered to the tumor area in an amount of about 0.1 to 1 mg, on a dry weight basis of the crosslinked gelatin gel, per 200 $mm^3$ of the tumor volume. This data amount corresponds to a human dose or 0.1 to 5 mg or 0.5 to 10 mg.

Example 4

Effect on Tumor Volume of Irradiation with Radiation Performed 72 Hours After Administration of the Sensitizer to Tumor 1. Method SCCVII tumor cells ($1.0 \times 10^5$ cells/animal) were implanted subcutaneously Into the right lower thigh of the mice in the same manner as in the "1. Method" section of Example 1. The mice were grouped as follows:
Group 1: Control group (receiving no sensitizer)
Group 2: KORTUC croup (receiving 100 µl of the sensitizer of Comparative Example 2)
Group 3: PI5-30 group (receiving the sensitizer of Formulation Example 1 in an amount of 0.6 mg, on a dry weight basis of MedGel)
Group 4: PI9-0.6 group (receiving the sensitizer of Formulation Example 2 in an amount of 0.6 mg, on a dry weight basis of MedGel)

At the stage of a tumor volume of about 200 to 250 mg, 100 µl of the sensitizer obtained in Comparative Example 2, or 30 µl of the sensitizer obtained in Formulation Example 1 was injected into each tumor. Because the sensitizer obtained in Formulation Example 2 was in the form of an elastic solid, the tumor area was incised and the sensitizer was implanted in an amount of 2 or 0.6 mg, on a dry weight basis of MedGel (crosslinked gelatin gel), per about 200 to 250 mg of the tumor volume.

Seventy-two hours after the administration of the sensitizer, the tumor was irradiated with radiation under the same conditions as in the "1. Method" section of Example 1, and the tumor volume on day 37 from the administration of the sensitizer (on day 34 from the irradiation with radiation) was measured.

2. Results

Figure 7:
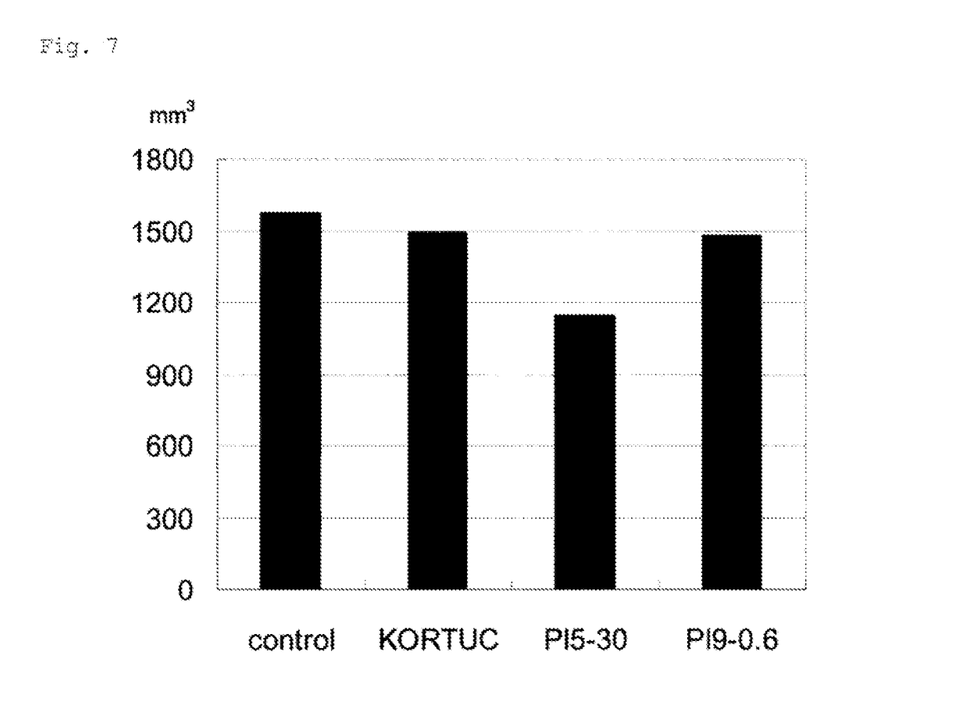
FIG. 7 shows the effect on tumor volume of irradiation with radiation performed 72 hours after the administration of each sensitizer to a tumor. The tumor volume was measured on day 37 after the administration of the sensitizer (on day 34 after irradiation with radiation). The control refers to a group that was only irradiated with radiation. KORTUC refers to a group to which KOURTUC was administered and that was irradiated with radiation. PI5-30 refers to a group to which 30 μl of the sensitizer in Formulation Example 1 was administered and that was irradiated with radiation. PI9-0.6 refers to a group to which the sensitizer of Formulation Example 2 was administered in an amount of 0.6 mg, on a dry weight basis of PI-9, and that was irradiated with radiation.

As shown in FIG. 7, no substantial difference was observed in tumor volume among the KORTUC group (KORTUC), PI9-0.6 group (PI9-0.6), and the control group (control). In contrast, an increase in tumor volume was inhibited in the PI5-30 group (PI5-30), compared to the other groups. These results suggest that a hydrogel comprising a crosslinked gelatin gel that is prepared from a gelatin having an isoelectric point of 4.5 to 5.5 is preferably used.

The embodiments of the invention in which an exclusive property or privilege is claimed are defined as follows:

1. A sensitizer comprising a combination of: (a) hydrogen peroxide at a concentration of 0.5 to 3.5 w/v % and (b) a hydrogel comprising a crosslinked gelatin gel prepared from a gelatin having an isoelectric point of 4.5 to 5, wherein the crosslinked gelatin gel is in a particulate form, the hydrogel is at a concentration of 0.5 to 10 w/v %, and the sensitizer is in an intratumoral injection form.

2. The sensitizer according to claim 1, wherein the crosslinked gelatin gel has a water content of 92 to 99.7%.

3. The sensitizer according to claim 2, which, in form of a final formulation, is administered in an amount of 0.1 to 10 mg on a dry weight basis of the crosslinked gelatin gel, per 200 $mm^3$ of the tumor volume.

4. The sensitizer according to claim 3, which, in form of a final formulation, is administered in an amount of 0.1 to 1 mg on a dry weight basis of the crosslinked gelatin gel, per 200 $mm^3$ of the tumor volume.

5. The sensitizer according to claim 1, wherein the hydrogen peroxide is at a concentration of 0.5 to 3.0 w/v % and the hydrogel is at a concentration of 1.67 to 5 w/v %.

6. The sensitizer according to claim 1, wherein the hydrogen peroxide is at a concentration of 0.5 to 2.0 w/v % and the hydrogel is at a concentration of 1.67 to 5 w/v %.

7. The sensitizer according to claim 1, wherein the hydrogen peroxide is at a concentration of 0.5 to 2 w/v % and the hydrogel is at a concentration of 1.67 w/v %.

* * * * *